United States Patent [19]
Sakaguchi et al.

[11] Patent Number: 5,846,211
[45] Date of Patent: Dec. 8, 1998

[54] OCCLUSAL FORCE-METER

[75] Inventors: Masao Sakaguchi; Junichi Yoshiike; Hiroaki Tsuruta; Hirofumi Abe, all of Tokyo, Japan

[73] Assignee: Nagano Keiki Seisakusho, Ltd., Tokyo, Japan

[21] Appl. No.: 805,643

[22] Filed: Feb. 27, 1997

[51] Int. Cl.$^6$ .................................................. A61B 5/103
[52] U.S. Cl. ............................ 600/590; 600/587; 433/71
[58] Field of Search ................................... 600/590, 587, 600/588, 589, 592; 73/379.02, 379.03, 379.09; 128/861; 433/71, 68, 70

[56] References Cited

U.S. PATENT DOCUMENTS

| | | | |
|---|---|---|---|
| 3,791,375 | 2/1974 | Pfeiffer | 73/172 |
| 4,488,873 | 12/1984 | Bloomfield et al. | 600/590 |
| 4,521,186 | 6/1985 | Wodlinger et al. | 600/590 |
| 4,592,727 | 6/1986 | Bloomfield | 600/590 |
| 4,976,618 | 12/1990 | Anderson | 600/590 |
| 5,353,800 | 10/1994 | Pohndorf et al. | 600/486 |
| 5,381,799 | 1/1995 | Hamilton et al. | 600/590 |

FOREIGN PATENT DOCUMENTS

57-170704 10/1982 Japan .
2-25379 7/1990 Japan .

Primary Examiner—Richard J. Apley
Assistant Examiner—Justine R. Yu
Attorney, Agent, or Firm—Birch, Stewart, Kolasch and Birch, LLP

[57] ABSTRACT

An occlusal force-meter 1 includes an occlusal force detecting portion 2 for detecting an occlusal force and a main body 3 for processing the detected signal obtained by the occlusal force detecting portion 2 to display the occlusal force measured value on a display 4. The occlusal force detecting portion 2 includes a transmitting portion (second pressure transmitting portion) 5 having diaphragm portions 7, 8 at an upper surface and/or a lower surface of one end portion 5f thereof. A pressure medium liquid L is filed therein, for transmitting the occlusal force added to the diaphragm portions 7, 8 to a pressure detector 9 disposed on the other end portion 5r thereof. A first pressure transmitting portion 10 is positioned between teeth T and the diaphragm portions 7, 8 at the time of occlusion of the tested person for adding the occlusal force to surfaces of the diaphragm portions 7, 8 perpendicularly through the pressure applied surfaces of the diaphragm portions 7, 8 perpendicularly through the pressure applied surfaces Fu, Fd abutted to outer surfaces of the diaphragm portions 7, 8.

19 Claims, 6 Drawing Sheets

OCCLUSAL FORCE-METER

BACKGROUND OF THE INVENTION

1. Field of the Invention

The present invention relates to an occlusal force-meter for measuring an occlusal force which is added to occlusal surfaces of the teeth due to the occlusion.

2. Description of the Relevant Art

Conventionally, as an occlusal force-meter for measuring an occlusal force, there are known an occlusion force measuring instrument shown in the official gazette of Japanese Utility Model Application Laid Open (Kokai) No. 57-170704, an occlusal force measuring device shown in the official gazette of Japanese Utility Model Publication (Kokoku) No. 2-25379 and the like.

Any one of such conventional occlusal force-meters directly detects an occlusal force by an occlusal force detecting portion using a force-electric transducer, obtains an occlusal force measured value by applying the detected signal obtained by the occlusal force detecting portion, and processing the detected signal at a main body thereof, and displays the occlusal force measured value on a display disposed on the main body.

In the occlusal force-meter of this kind, a portion to be bitten by the teeth (the bitten portion) is preferably made thin as much as possible, in order to measure the occlusal force accurately and raise the usability.

However, since the force-electric transducer (load cell) for detecting a large force such as an occlusal force is usually considerably thick, the tested person must bite the thick bitten portion in the mouth. This causes problems in that the usability is deteriorated, and the occlusal force cannot be measured accurately and precisely.

SUMMARY OF THE INVENTION

It is therefore an object of the present invention to provide an occlusal force-meter which is capable of measuring an occlusal force always accurately irrespective of a position and an angle of a tooth, a measured condition and the like.

It is another object of the present invention to provide an occlusal force-meter which makes it easy to bite the bitten portion by making the same thin, to thereby raise the usability, in addition, which is capable of measuring the occlusal force precisely.

It is still another object of the present invention to provide an occlusal force-meter which is made more sanitary by making it more waterproof and preventing adhesion of contaminations, refuses and the like.

In order to attain the above objects, the present invention provides an occlusal force-meter 1 comprising an occlusal force detecting portion 2 for detecting an occlusal force, and a main body 3 for processing the detected signal obtained by the occlusal force detecting portion 2 to display the occlusal force measured value on a display 4, characterized in that the occlusal force detecting portion 2 is comprised of a pressure transmitting portion (second pressure transmitting portion) 5 having diaphragm portions 7, 8 at an upper surface and/or a lower surface of one end portion 5f thereof, and a pressure medium liquid L filled therein, for transmitting the occlusal force added to the diaphragm portions 7, 8 to a pressure detector 9 disposed on the other end portion 5r thereof; and a first pressure transmitting portion 10 disposed between teeth T, . . . and the diaphragm portions 7, 8 at the time of occlusion of the tested person, for adding the occlusal force to surfaces of the diaphragm portions 7, 8 perpendicularly through pressure applied surfaces Fu, Fd abutted to outer surfaces of the diaphragm portions 7, 8.

On this occasion, the first pressure transmitting portion 10 comprises an upper arm portion 11 and a lower arm portion 12 which are connected to each other at rear ends thereof, and the pressure applied surfaces Fu, Fd are disposed on the leading ends of the upper arm portion 11 and the lower arm portion 12. Then, a part or all of the upper arm portion 11 and/or the lower arm portion 12 may be made of spring material, then the rear ends of the upper arm portion 11 and the lower arm portion 12 are connected to each other, or the rear ends of the upper arm portion 11 and the lower arm portion 12 may be rotatably connected to each other by a hinge portion 13.

Also, the occlusal force detecting portion 2 and the main body 3 are flexibly connected to each other through an elastic connecting portion 14. On this occasion, an elongated portion 15 is disposed unitedly on a rear end of any one of an upper arm portion 11 and a lower arm portion 12 which are made of spring material, the elongated portion 15 can be used as the elastic connecting portion 14 by connecting a rear end of the elongated portion 15 with the main body 3.

Further, the second pressure transmitting portion 5 is comprised of a flat pressure receiving tank 21 having an upper surface and/or a lower surface thereof formed as the diaphragm portions 7, 8, and said pressure detector 9 has a pressurized room 28 therein, and an inside of the pressure receiving tank 21 and the pressurized room 28 are communicated/connected to each other by the pressure transmitting pipe 23. Meanwhile, there is provided a flexible protecting case 16 for covering the occlusal force detecting portion 2. Preferably, the protecting case 16 is made of vinyl chloride.

The main body 3 has a function of sounding a buzzer when the detected occlusal force is of the maximum value to display the maximum value on the display 4, and has a function (standard mode) of storing a plurality of measured values to display the measured values, the average value, and the maximum value on the display 4, and then a function of sounding a buzzer when the detected occlusal force reaches to a predetermined set value.

Whereby, if the tested person bites the portion (bitten portion) on which the diaphragm portions 7, 8 are disposed, by the teeth T, . . . , the occlusal force is added to the pressure applied surfaces Fu, Fd perpendicularly to the surfaces of the diaphragm portions 7, 8 and uniformly, due to the presence of the first pressure transmitting portion 10. In concrete terms, since the first pressure transmitting portion 10 comprises an upper arm portion 11 and a lower arm portion 12 which are connected to each other at rear ends thereof, and the pressure applied surfaces Fu, Fd are disposed on the leading ends of the upper arm portion 11 and the lower arm portion 12, the respective pressure applied surfaces Fu, Fd are displaceable relatively perpendicularly to the surfaces of the diaphragm portions 7, 8. Therefore, if there is no first pressure transmitting portion 10, that is, there is only the pressure receiving disk abutted to the surfaces of the diaphragm portions 7, 8, there is exerted a bad effect in that the occlusal force is not added to the diaphragm portions 7, 8 perpendicularly and uniformly due to the position and the angle of the teeth T, . . . , and the measuring condition and the like. However, such a bad effect is resolved due to the function of the first pressure transmitting portion 10, whereby an accurate measurement is always carried out.

Meanwhile, the occlusal force added to the diaphragm portions 7, 8 is transmitted to the pressure detector 9 disposed on the other end 5r of the second pressure transmitting portion 5 through the pressure medium liquid L, then the occlusal force is detected by the pressure detector 9. Then, the main body 3 processes the detected signal obtained from the pressure detector 9, thereby obtaining the occlusal force measured value, which is displayed on the display 4. On this occasion, since the pressure detector 9 is not at a location corresponding to the diaphragm portions 7, 8 which are to be bitten by the tested person, the occlusal force detecting portion 2 which is the bitten portion can be made extremely thin. However, the occlusal force detecting portion 2 is made easy to bite, thereby raising the usability and enabling the measurement of the accurate and precise occlusal force.

Moreover, since the occlusal force detecting portion 2 and the main body 3 are connected to each other through the elastic connecting portion 14, they become flexible, thereby raising the usability, and in particular, the elongated portion 15 is disposed unitedly on the rear end of one of the upper arm portion 11 and the lower arm portion 12 which are made of spring material, the elongated portion 15 is used as the elastic connecting portion 14 by connecting the rear end of the elongated portion 15 with the main body 3, thereby making the construction simple, and realizing the reduction in cost, and making it hard to break an intermediate portion between the occlusal force detecting portion 2 and the main body 3. Further, it is ensured that the force detecting portion 2 is waterproof due to the soft protecting case 16 covering the occlusal force detecting portion 2, and particularly, if the protecting case 16 is made of vinyl chloride, an impression of the teeth marked on the protecting case 16 is easily restored to the former state by, for example, dipping it a hot water, and so on.

Further objects and advantages of the present invention will be apparent from the following description of the preferred embodiments of the present invention as illustrated in the appended drawings. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Preferable embodiments according to the present invention will be described hereinafter with reference to the appended drawings. The appended drawings do not aim to specify the present invention, but aim to help the understanding of the present invention. Also, detail explanation will not be made to well known parts so as not to make the present invention ambiguous.

Figure 5:
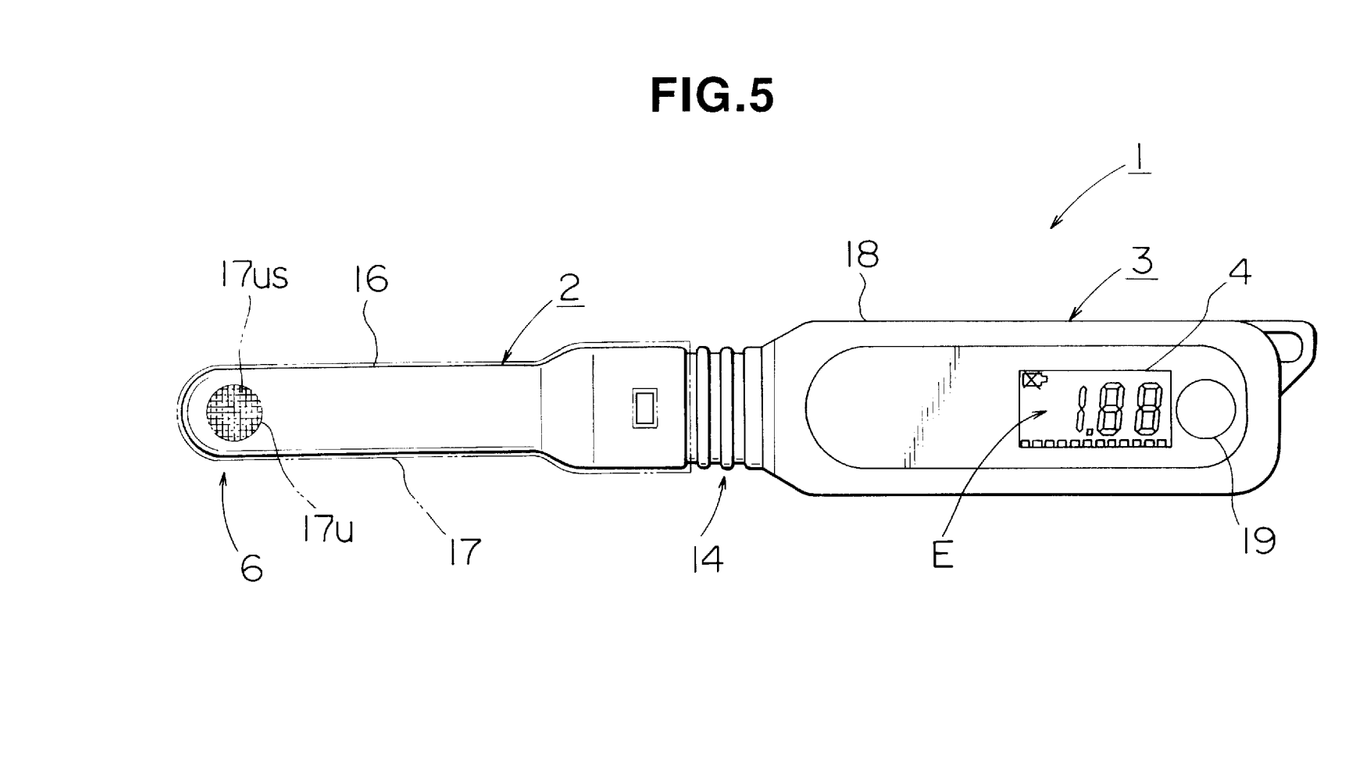
FIG. 5 is an outside appearance plan view of the occlusal force-meter.

First, an outside appearance configuration of an occlusal force-meter 1 according to the embodiment will now be described with reference to FIG. 5.

An occlusal force-meter 1 is comprised of a main body 3 and an occlusal force detecting portion 2 which are united with each other. The main body 3 has a housing portion 18 serving as a grip which can be grasped by the hand. The housing portion 18 has an electronic circuit, a battery and the like built-in. Meanwhile, there are disposed on an upper surface of the housing portion 18 a display 4 for digital-displaying an occlusal force measured value, an electric power key (function key) 19 and the like. Then, the occlusal force detecting portion 2 is disposed unitedly on a front end of the housing portion 18 through an elastic connecting portion 14.

Next, a description of the occlusal force detecting portion 2 and the elastic connecting portion 14 which constitutes a main part of the present invention will be described hereinafter with reference to FIG. 1 to FIG. 4.

Figure 3:
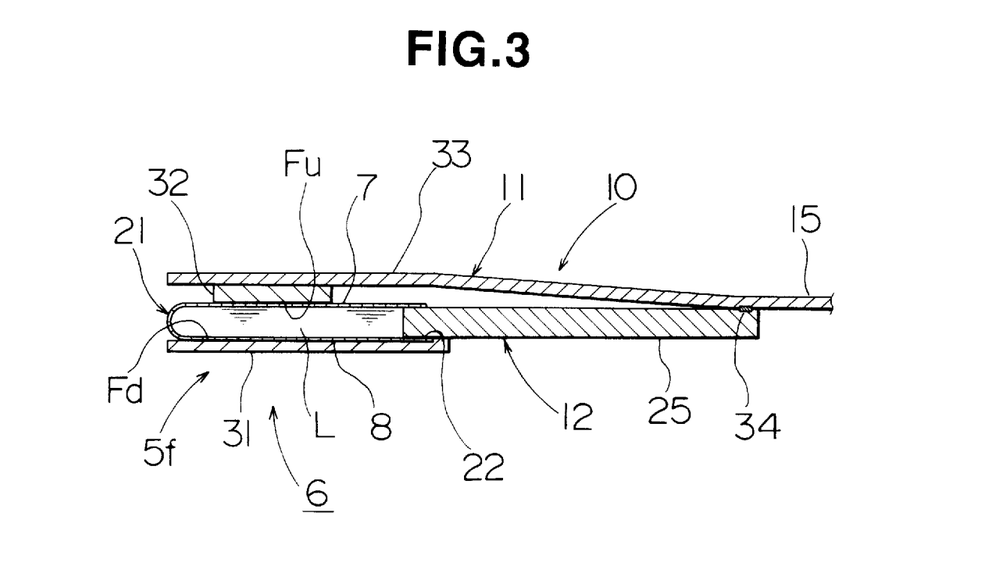
FIG. 3 is a sectional side view of a first pressure transmitting portion in the occlusal force sectional detecting portion of the occlusal force-meter.
Figure 4:
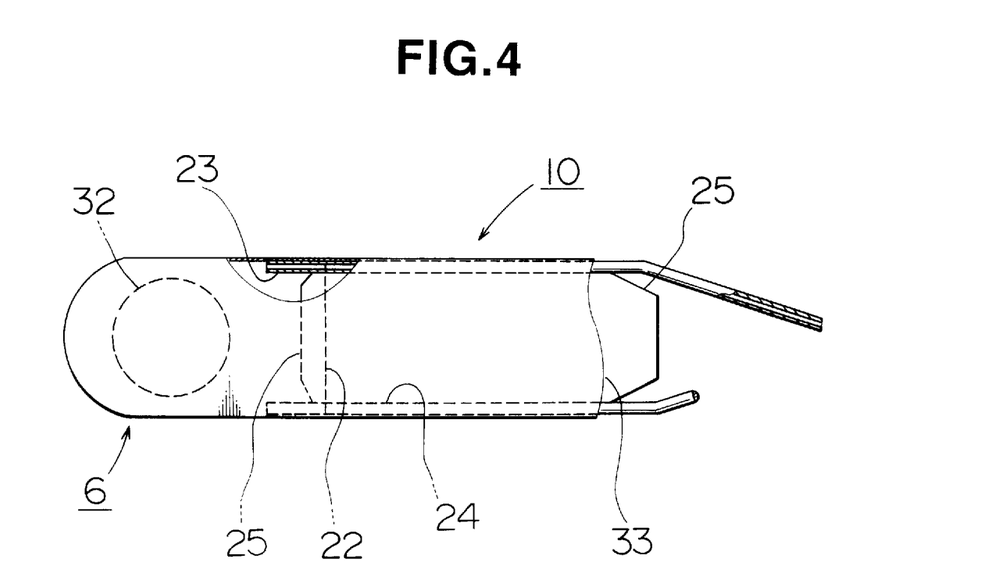
FIG. 4 is a partially sectional plan view of the first pressure transmitting portion shown in FIG. 3.

The occlusal force detecting portion 2 has a pressure receiving tank 21 built-in at a leading end thereof. The pressure receiving tank 21 is made of a hollow stainless steel member shaped in a flat, which has an opening portion 22 at a rear end thereof. An upper surface portion and a lower surface portion of the pressure receiving tank 21 are made thin, which serve as diaphragm portions 7, 8, respectively. Further, leading ends of a pressure transmitting pipe 23, an auxiliary pipe 24 and an attaching plate 25 are inserted into the opening portion 22, as shown in FIG. 3 and FIG. 4, then they are fixed thereto by brazing and the like, which results in closing of the opening portion 22. Moreover, the leading end of the auxiliary pipe 24 is closed.

Figure 1:
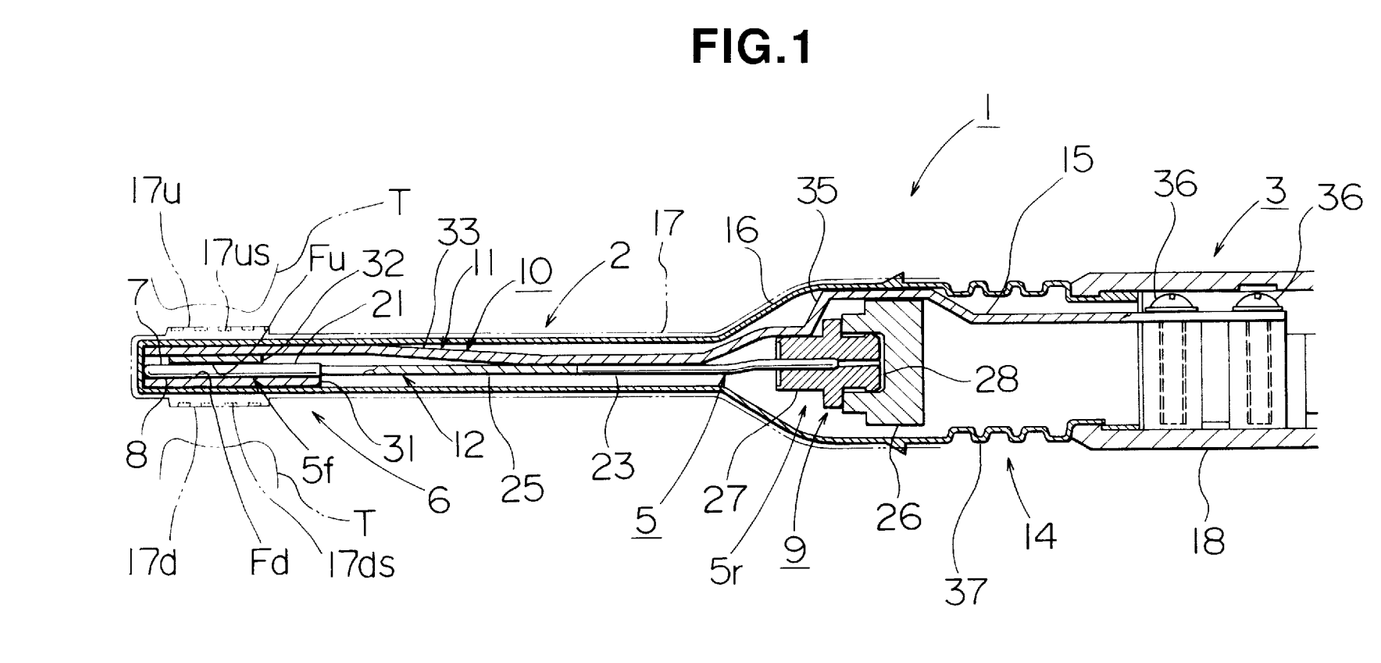
FIG. 1 is a partial sectional side view of an occlusal force detecting portion in an occlusal force-meter according to the present invention.

Meanwhile, the pressure detector 9 is disposed on a rearward position distant from the pressure receiving tank 21. The pressure detector 9 is comprised of a detector main body 26 and a coupler 27 which are connected to each other with a pressurized space 28 provided therebetween. Moreover, a rear end of the pressure transmitting pipe 23 is connected to the pressure detector 9, then an inside of the pressure transmitting pipe 23 is communicated with the pressurized space 28. Reference numeral 30 designates an auxiliary pipe communicated with the pressurized space 28, then a leading end of the auxiliary pipe 30 is closed.

According to such a construction, the pressure receiving tank 21, the pressurized space 28, the pressure transmitting pipe 23, the auxiliary pipe 24 and the auxiliary pipe 30 are communicated with one another at insides thereof, into which a pressure medium liquid L such as propylene glycol and the like are filled. Each of the pressure transmitting pipe 23, the auxiliary pipe 24 and the auxiliary pipe 30 is comprised of a capillary tube with such a size as to minimize an amount of liquid. Also, the auxiliary pipe 24 and the auxiliary pipe 30 are used for filling the pressure medium liquid L into the above-mentioned inside.

Whereby, the occlusal force added to the diaphragm portions 7, 8 is transmitted to the pressure detector 9 through the pressure medium liquid L, then sensed as an electric signal by the pressure detector 9. A metal diaphragm type pressure sensor can be used for the pressure detector 9. Such a construction mainly including the pressure receiving tank 21, the attaching plate 25, the auxiliary pipe 24, the auxiliary pipe 30 and the pressure transmitting pipe 23 constitute a second pressure transmitting portion 5.

The base plate 31 is abutted to a lower diaphragm portion 8, in the drawing, which is fixed to the attaching plate 25 at a rear end thereof. Whereby the abutting surface of the base plate 31 to the diaphragm portion 8 constitutes a pressure applied surface Fd, then the attaching plate 25 and the base plate 31 constitute a lower arm portion 12 in the drawing.

A circle pressure receiving disk 32 is abutted to an upper diaphragm portion 7 in the drawing period, furthermore a leading end of the lever plate 33 is abutted onto the pressure receiving disk 32. The lever plate 33 is comprised of an elongated member of spring use stainless steel (spring material). An intermediate portion of the lever plate 33 and the other end of the attaching plate 25 are fixed to each other by a welding portion 34 as shown in FIG. 3. Whereby, the abutting surface of the pressure receiving disk 32 to the diaphragm portion 7 constitutes a pressure applied surface Fu, then the fore side portion (on a side of the pressure receiving disk 32) of the pressure receiving disk 32 and the lever plate 33 with respect to the welding portion 34 constitute an upper arm portion 11 in the drawing. On this occasion, the surface of the lever plate 33 opposing to the diaphragm portion 7 is folded at suitable positions so as to be in parallel with the diaphragm portion 7. Moreover, the occlusal force detecting portion 2 constitutes a bitten portion at a location corresponding to the diaphragm portions 7, 8.

Therefore, rear ends of the upper arm portion 11 and the lower portion 12 are connected to each other, whereas leading ends thereof are displaceable relatively. The upper arm portion 11 and the lower arm portion 12 constitute a first pressure transmitting portion 10 positioned between the teeth T, . . . of the tested person at the time of the occlusion and the diaphragm portions 7, 8, for applying the occlusal force on the surfaces of the diaphragm portions 7, 8 through the pressure applied surfaces Fu, Fd abutted to outer surfaces of the diaphragm portions 7, 8, when the tested person bites the bitten portion 6. Moreover, since the lever plate 33 constituting the upper arm portion 11 has a predetermined elasticity, the elastic force acts as an error in the occlusal force. This error is canceled due to the signal processing (zero point adjustment) of the detected signal at the main body 3.

A portion of the lever plate 33 which is located on a rear side of the welding portion 34 constitutes an elongated portion 15. The elongated portion 15 has a front half portion formed flexibly as a detector attaching portion 35 and a rear half portion used as a flexible elastic connecting portion 14.

The pressure detector 9 is attached and fixed to the detector attaching portion 35 and the rear end of the elongated portion 15 is fixed to an inner leading end of the housing portion 18 by screws 36, . . .

Figure 2:
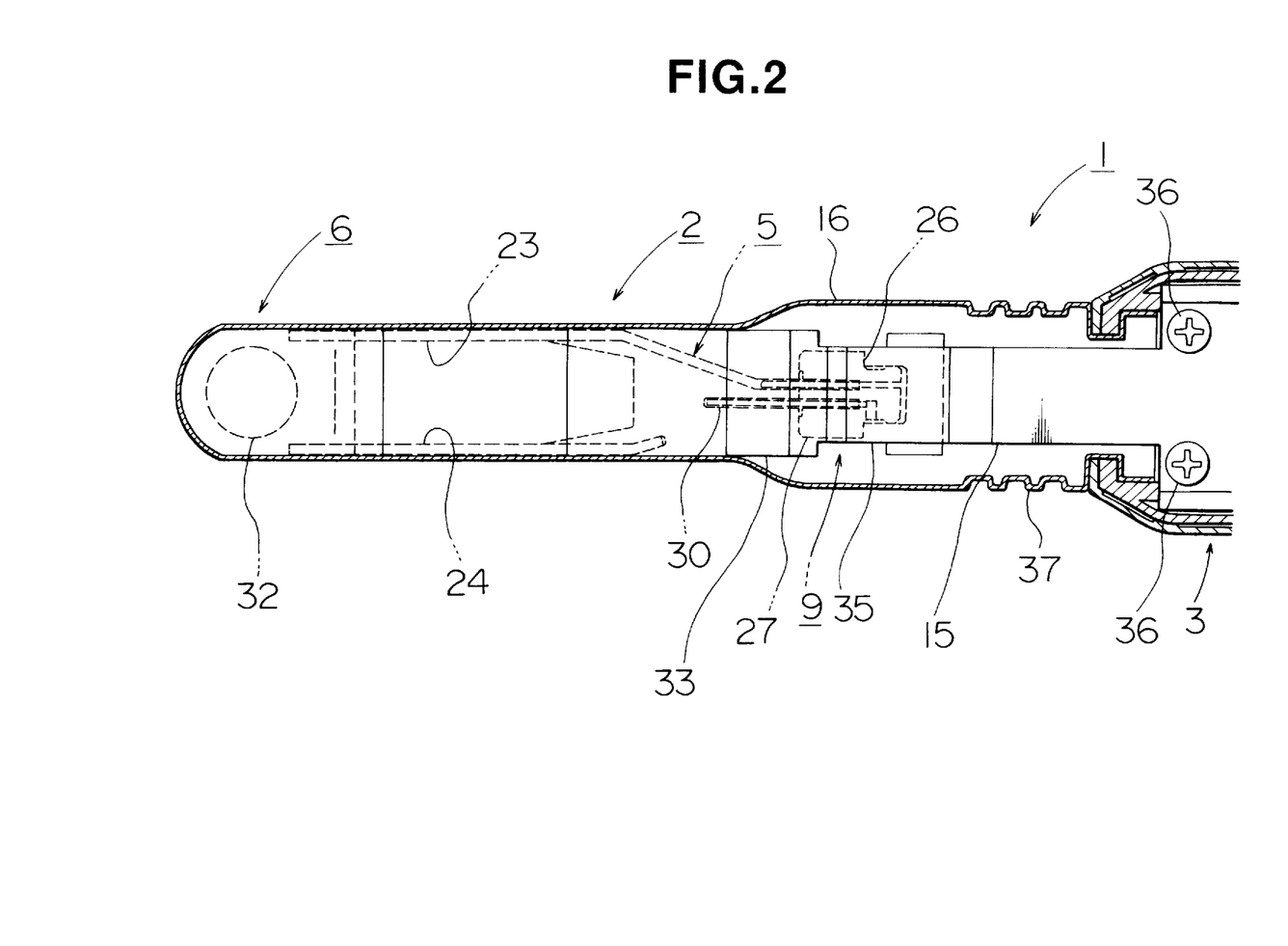
FIG. 2 is a partial plan view of a protecting case and a housing portion of the occlusal force detecting portion in the occlusal force-meter.

Further, reference numeral 16 denotes a soft protecting case 16 made of vinyl chloride, which has an opening at a rear end thereof. The protecting case 16 covers all of the inside mechanism of the occlusal force detecting portion 2. The protecting case 16 is corrugated so as to be extended or extracted according to the deformation of the elongated portion 15.

A method of using occlusal force-meter 1 according to the embodiment of the present invention will be described hereinbelow with reference to the drawings.

The tested person holds the housing portion 18, then enters into the mouth the bitten portion 6 with a detachable (disposable) cap 17. The disposable cap 17 is an accessory detachable to the occlusal force detecting portion 2 as shown by imaginary lines in FIG. 1 and FIG. 5, and is made, as one-body, of e.g. a flexible synthetic resin. The disposable cap 17 has thickness portions 17$u$, 17$d$ protruding outward thereby directly abutting the teeth at portions corresponding to the diapragm portions 7, 8 Non-slip portions 17$us$, 17$ds$ having irregularities are formed on surfaces of the thickness portions 17$u$, 17$d$. After positioning it, if he or she bites the bitten portion 6 with the teeth T, . . . with all one's force as shown by reference symbol T in FIG. 1, the occlusal force exposed on this occasion is transmitted to the diaphragm portions 7, 8 of the second pressure transmitting portion 5 through the first pressure transmitting portion 10. On this occasion, the first pressure transmitting portion 10 is so constructed that leading ends of the upper arm portion 11 and the lower arm portion 12 are capable of being displaceable relatively since the rear ends thereof are connected to each other. Accordingly, the occlusal force is applied to the surfaces of the diaphragm portions 7, 8 perpendicularly and uniformly, which realizes an accurate measurement.

Meanwhile, the occlusal force applied to the diaphragm portions 7, 8 is further applied to the pressure medium liquid L in the occlusal force detecting portion 2. The occlusal force, which is transmitted to the detector main body 26 of the pressure detector 9 through the pressure medium liquid L within the pressure transmitting pipe 23 and the diaphragm 8, is converted to an electrical signal (detected signal) by the detector main body 26. Then, the detected signal obtained from the detector main body 26 is subjected to a correction and a process such an analogue-digital conversion and the like by a signal processing section (not shown) in the main body 3 to thereby be converted to a measured occlusal force value, then displayed on the display 4.

On this occasion, the main body 3 performs the measurement while selecting a standard mode or a set mode. The standard mode and the set mode can be selected by the function key 19. In case of the standard mode, a buzzer sounds when the detected occlusal force is of the maximum value, then the maximum value is displayed on the display 4 and memorized in a memory. Then, ten maximum measured values are stored in the memory, then the measured values, the average value, and the maximum value are displayed on the display 4 in order. On the other hand, in case of the set mode, the set value (for example, 5 kgf) is set previously. During measurement, the buzzer sounds when the detected occlusal force reaches the set value. According to such a set mode, it can be easily determined whether or not the set occlusal force can be obtained, or whether or not the adjustment of an artificial tooth is normal. The limit value (for example, 70 kgf) is set in any of the modes, then the alarm is given by continuously sounding the buzzer if the measured value is over the limit value.

Figure 6:
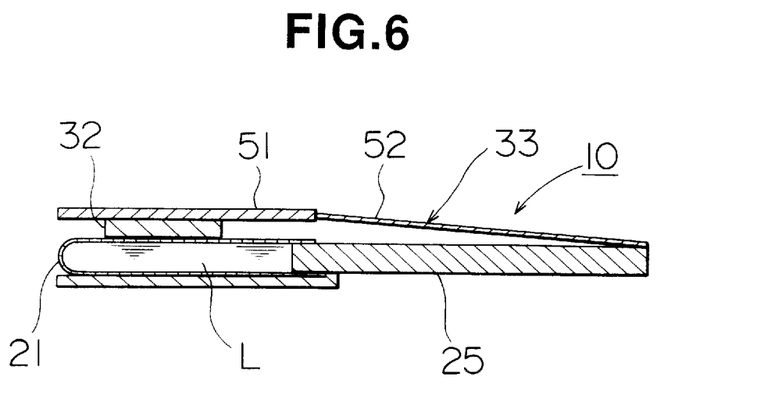
FIG. 6 is a sectional side view of the first pressure transmitting portion according to a variant embodiment of the present invention.
Figure 7:
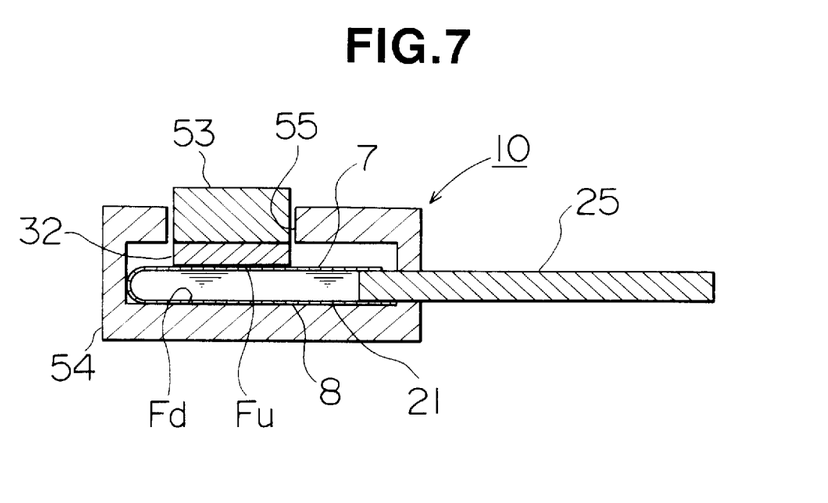
FIG. 7 is a sectional side view of the first pressure transmitting portion according to another variant embodiment of the present invention.
Figure 8:
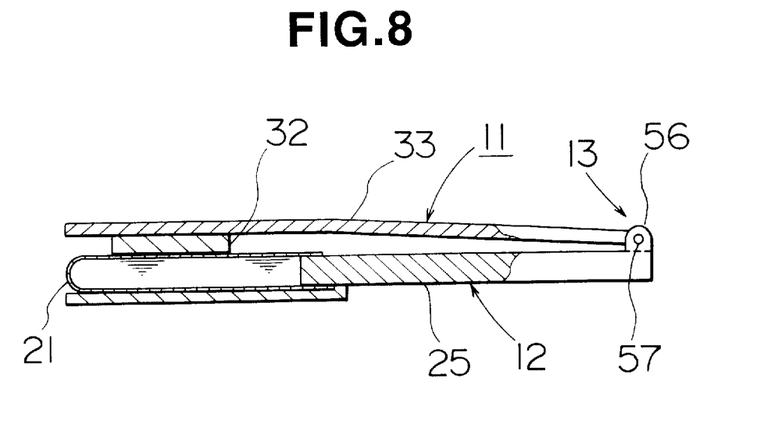
FIG. 8 a partial sectional side view of the first pressure transmitting portion according to another variant embodiment of the present invention.
Figure 9:
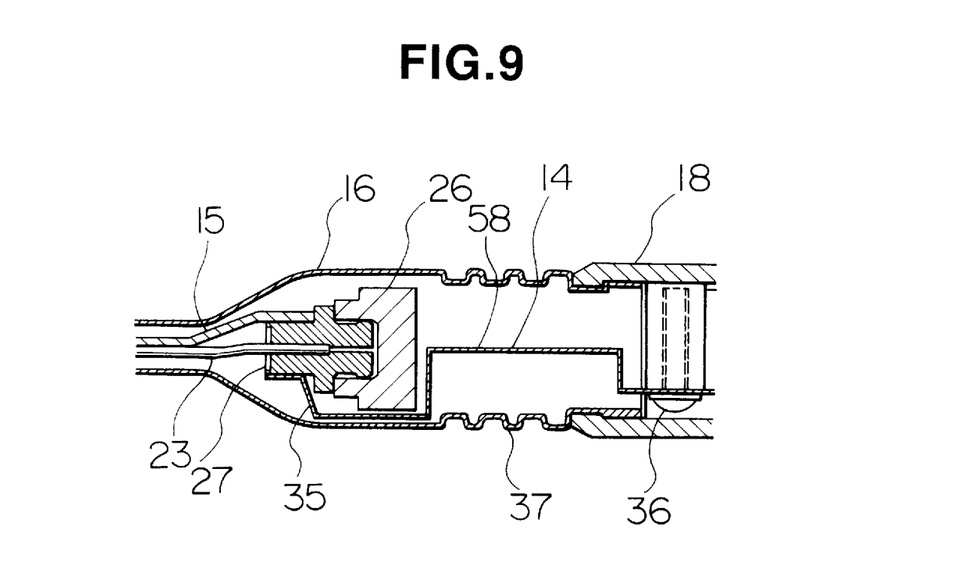
FIG. 9 is a sectional side view of an elastic connecting portion according to the variant embodiment of the present invention.
Figure 10:
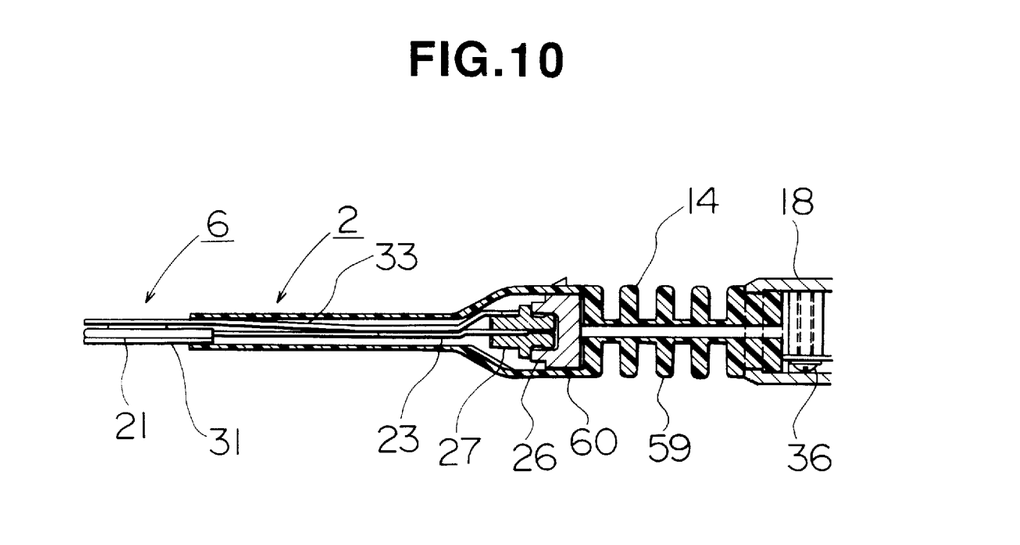
FIG. 10 is a sectional side view of an elastic connecting portion according to the another variant embodiment of the present invention.

Next, a variant embodiment of the present invention will be described with reference to FIG. 6 to FIG. 10. FIG. 6 to FIG. 8 are variant embodiments of the first pressure transmitting portion 10, and FIG. 9 and FIG. 10 are variant embodiments of the elastic connecting portion 14, respectively.

FIG. 6 shows a variant embodiment of the lever plate 33 shown in FIG. 3. This variant embodiment is constructed by combining a fore pressing plate 51 and with a rear leaf spring plate 52 which are formed individually, when constituting the lever plate 33. According to such a construction, the pressing plate 51 and the leaf spring plate 52 are made different from each other in material, thickness, contour and the like. For example, the pressing plate 51 made of a rigid material can be abutted to the pressure receiving disk 32, then supported by the leaf spring plate 52 having a suitable elasticity, which is fixed to the attaching plate 25.

Also, FIG. 7 shows another variant embodiment of the lever plate 33 shown in FIG. 3. This embodiment is comprised of a guided block 53 having a uniform thickness fixed to the pressure receiving disk 32 abutted to the diaphragm portion 7, and a guiding member 54 having a guiding slit 55 for guiding the guided block 53 in a perpendicular direction to the surface of the diaphragm portion 7. The guiding member 54 has a pressure applied surface Fd abutted to the diaphragm 8. According to such a construction also, the pressure applied surfaces Fu and Fd can be displaceable relatively perpendicularly to the surfaces of the diaphragm portions 7, 8. If the thickness of the pressure receiving disk 32 is made uniform, the guided block 53 can be omitted.

Further, FIG. 8 shows still another variant embodiment of the lever plate 33 shown in FIG. 3. This embodiment is comprised of the upper arm portion 11 and the lower arm portion 12 rotatably connected to each other at rear ends thereof. That is, the bearing bracket portion 56 disposed on the rear end of the attaching plate 25 and a bearing portion disposed on the rear end of the lever plate 33 are rotatably connected to each other through a shaft portion 57. Although the construction is complicated compared with the embodiment shown in FIG. 3, there is an advantage that the elastic force due to the lever plate 33 does not exert a bad influence upon the measured value. Moreover, the lever plate 33 need not have the elasticity.

In FIG. 9, the lever plate 33 and the elastic connecting portion 14 (and the detector attaching portion 35) are formed individually. The elongated portion 15 is shortened compared with the embodiment shown in FIG. 1, the pressure detector 9 is attached to the rear end of the elongated portion 15, a fore end of a connecting plate 58 formed by uniting the elastic connecting portion 14 with the detector attaching portion 35 as one body is attached to the pressure detector 9, further a rear end of the connecting plate 58 is fixed to the housing portion 18. Whereby, the elastic connecting portion 14 and the lever plate 33 can be easily made different from each other in material, thickness, and contour and the like.

In FIG. 10, the elastic connecting portion 14 is constituted by using a connecting member 59 made of elastic plastic instead of the connecting plate 58 in the variant embodiment shown in FIG. 9, which holds the pressure detector 9 by the containing portion 60 disposed on a fore end of the connecting member 59. On this occasion, the containing portion 60 serves as the protecting case 16 mentioned above.

The embodiments of the present invention are described above in detail. However, the present invention is not restricted to such embodiments. The detailed construction, contour, material and the like can be optionally modified as long as they are not deviated from the gist of the present invention. Further, omissions and the additions can be made as the occasion demands.

For example, although the diaphragm portions are disposed on an upper surface and a lower surface in the above embodiment, any one of them will suffice. Further, the attaching plate constituting the lower arm may have the elasticity.

We claim:

1. An occlusal force-meter comprising:
   an occlusal force detecting portion for detecting an occlusal force applied by teeth of a user and for sending a signal in response thereto;
   a main body for processing said signal sent by said occlusal force detecting portion in order to display a value of the occlusal force;
   said occlusal force detecting portion including a first pressure transmitting portion and a second pressure transmitting portion, said second pressure transmitting portion having diaphragm portions at an upper surface and a lower surface of one end portion of said second pressure transmitting portion and a pressure liquid medium filled therein for transmitting said applied occlusal force to a pressure detector disposed on a second end portion thereof, said first pressure transmitting portion being located adjacent an upper and a lower surface of said diaphragm portions, for being disposed between the teeth of a user, said first pressure transmitting portion further including pressure applied surfaces for transmitting said applied occlusal force generally perpendicularly to said upper and lower surfaces of said diaphragm portions.

2. An occlusal force-meter as claimed as in claim 1, wherein said occlusal force detecting portion and the main body portion are formed as one body.

3. An occlusal force-meter as claimed in claim 1, wherein said first pressure transmitting portion further comprises an upper arm portion and a lower arm portion, each having first ends connected to each other and second ends adjacent to said diaphragm portions, said pressure applied surfaces being disposed on said second ends of said upper and lower arm portions, respectively.

4. An occlusal force-meter as claimed as in claim 3, wherein at least a portion of said upper arm portion and said lower arm portion is made of spring material.

5. An occlusal force-meter as claimed as in claim 3, wherein said first ends of said upper arm portion and said lower arm portion are pivotally connected to each other by a hinge portion.

6. An occlusal force-meter as claimed in claim 3, wherein said occlusal force detecting portion and said main body are flexibly connected to each other through an elastic connecting portion, said elastic connecting portion including an elongated portion extending from said first end of said upper arm portion or said first end of said lower arm portion and connecting to said maim body.

7. An occlusal force-meter as claimed in claim 6, wherein said elongated portion extends around said pressure detector and across said flexible portion and connects to said main body.

8. An occlusal force-meter as claimed as in claim 1, wherein said occlusal force detecting portion and said main body are flexibly connected to each other through an elastic connecting portion.

9. An occlusal force-meter as claimed as in claim 8 wherein said elastic connecting portion includes an elongated portion on said first end of said upper arm portion or a first end of said lower arm portion, said elongated portion made of a spring material.

10. An occlusal force-meter as claimed as in claim 1, wherein said second pressure transmitting portion is comprised of a flat pressure receiving tank formed as said diaphragm portions, and said pressure detector has a pressurized space therein, and an inside of said pressure receiving tank and said pressurized space are communicated with each other by a pressure transmitting pipe.

11. An occlusal force-meter as claimed as in claim 1, wherein a flexible protecting case covers said occlusal force detecting portion.

12. An occlusal force-meter as claimed as in claim 11, wherein said protecting case is made of vinyl chloride.

13. An occlusal force-meter as claimed as in claim 1, wherein said main body sounds a buzzer when said detected occlusal force reaches a maximum value and displays said maximum value on said display.

14. An occlusal force-meter as claimed as in claim 13, wherein said main body has a function of storing a plurality of measured values in order to display the measured values in order, the average value, and the maximum value on said display.

15. An occlusal force-meter as claimed as in claim 1, wherein said main body has a function of sounding a buzzer when said detected occlusal force reaches a predetermined set value.

16. An occlusal force-meter as claimed as in claim 15, wherein the disposable cap has thickness portions protruding outwardly for directly abutting the teeth, said thickness portions being adjacent to the diaphragm portions.

17. An occlusal force-meter as claimed as in claim 16, wherein non-slip portions having an irregularity are formed on surfaces of the thickness portions.

18. An occlusal force-meter as claimed as in claim 1, wherein a disposable cap is provided detachable to the occlusive force detecting portion.

19. An occlusal force-meter as claimed as in claim 18, wherein said disposable cap is made of a flexible synthetic resin.

* * * * *